United States Patent [19]
Barrett

[11] Patent Number: 5,989,209
[45] Date of Patent: *Nov. 23, 1999

[54] GROOVED PHACO-EMULSIFICATION NEEDLE

[75] Inventor: Graham D. Barrett, City Beach, Australia

[73] Assignee: Oversby Pty Ltd., West Perth, Australia

[ * ] Notice: This patent is subject to a terminal disclaimer.

[21] Appl. No.: 08/884,904

[22] Filed: Jun. 30, 1997

Related U.S. Application Data

[63] Continuation of application No. 08/486,861, Jun. 7, 1995, Pat. No. 5,718,676.

[30] Foreign Application Priority Data

Sep. 2, 1994 [AU] Australia ............................ PM7844/94

[51] Int. Cl.[6] .................................................. A61B 1/30
[52] U.S. Cl. ............................ 604/22; 604/272; 606/107
[58] Field of Search ............................ 604/22, 192, 272; 601/2; 606/107, 169

[56] References Cited

U.S. PATENT DOCUMENTS

| | | |
|---|---|---|
| 3,386,438 | 6/1968 | Stevens . |
| 3,589,363 | 6/1971 | Banke et al. ............................ 128/276 |
| 4,320,761 | 3/1982 | Haddad .................... 128/305 |
| 4,515,583 | 5/1985 | Sorich ........................ 604/22 |
| 4,634,419 | 1/1987 | Kreizman et al. .................... 604/22 |
| 4,634,420 | 1/1987 | Spinosa et al. ............................ 604/22 |
| 4,634,717 | 1/1987 | Cook et al. ................................ 604/22 |
| 4,689,040 | 8/1987 | Thompson ............................ 604/22 |
| 4,804,364 | 2/1989 | Dieras et al. ............................ 604/22 |
| 4,808,154 | 2/1989 | Freeman .................................. 604/22 |
| 4,816,018 | 3/1989 | Parisi ...................................... 604/22 |
| 4,959,049 | 9/1990 | Smirmaul ................................. 604/22 |
| 5,011,471 | 4/1991 | Miyazaki et al. ........................ 604/22 |
| 5,038,756 | 8/1991 | Kepley ..................................... 128/24 |
| 5,071,421 | 12/1991 | Stahl . |
| 5,139,504 | 8/1992 | Zelman ..................................... 606/127 |
| 5,151,099 | 9/1992 | Young et al. .............................. 606/27 |
| 5,163,433 | 11/1992 | Kagawa et al. ..................... 128/660.01 |
| 5,178,605 | 1/1993 | Imonti ....................................... 604/22 |
| 5,188,589 | 2/1993 | Wypych et al. .......................... 604/22 |
| 5,199,943 | 4/1993 | Wypych .................................... 604/22 |
| 5,205,817 | 4/1993 | Idemoto et al. .......................... 604/22 |
| 5,213,569 | 5/1993 | Davis ....................................... 604/22 |
| 5,231,569 | 7/1993 | Davis . |
| 5,242,385 | 9/1993 | Strukel .................................... 604/22 |
| 5,282,786 | 2/1994 | Ureche .................................... 604/22 |
| 5,286,256 | 2/1994 | Mackool ................................. 604/22 |
| 5,300,084 | 4/1994 | Johnson . |
| 5,354,265 | 10/1994 | Mackool . |
| 5,464,389 | 11/1995 | Stahl ....................................... 604/22 |
| 5,718,676 | 2/1998 | Barrett . |

FOREIGN PATENT DOCUMENTS

| | | |
|---|---|---|
| 2466994 | 5/1981 | France . |
| 53855 | 2/1967 | Germany . |
| 53 855 | 11/1967 | Germany . |
| 3323867 A1 | 1/1985 | Germany .................. A61B 17/06 |
| 332387 | 1/1985 | Germany . |
| 602176 | 3/1978 | U.S.S.R. ........................ A61B 17/24 |
| 1066583-A | 1/1984 | U.S.S.R. ........................ A61B 17/24 |
| 1715328-A1 | 2/1992 | U.S.S.R. ........................ A61B 17/32 |
| WO 93/15703 | 8/1993 | WIPO ............................. A61F 17/00 |

*Primary Examiner*—Mark Bockelman
*Attorney, Agent, or Firm*—Fish & Neave; Nicola A. Pisano

[57] ABSTRACT

A phaco-emulsification needle is provided for use with a plastic or elastomeric sleeve, the needle having a mid-region portion defining a plurality of outwardly extending projections forming longitudinally-oriented grooves that provide adequate irrigant flow rates to the anterior chamber of the eye, even when the entry wound compresses the sleeve against the outer surface of the needle, thereby reducing the risk of collapse of the anterior chamber due to inadequate irrigant flow and reducing the risk of excessive heat transmission to the entry wound.

23 Claims, 5 Drawing Sheets

GROOVED PHACO-EMULSIFICATION NEEDLE

This is a continuation of application Ser. No. 08/486,861, filed Jun. 7, 1995, entitled "Grooved Phaco-Emulsification Needle" now U.S. Pat. No. 5,718,676.

FIELD OF THE INVENTION

The present invention relates generally to phaco-emulsification needles and more particularly to needles that provide improved irrigation and reduced risk of corneal or scleral tissue damage.

BACKGROUND OF THE INVENTION

Occurrence of the disease known as cataracts, in which the lens of the eye becomes clouded, is common, and can lead to blindness. It has become accepted practice to alleviate this condition by surgically removing the cataract-effected lens and replacing it by an artificial intraocular lens.

The cataract-effected lens is usually removed by manual extraction or phaco-emulsification. Manual extraction requires expression of the nucleus of the lens through a wound of about 12 mm in length.

The technique known as phaco-emulsification, as described, for example, in U.S. Pat. No. 3,589,363, enables removal of a cataract-effected lens through a much smaller incision of about 2.5–4 mm, for example, 3.2 mm. This is accomplished using high frequency ultrasound energy, typically of 40 kHz frequency, that is transmitted by a phaco-emulsification needle to fragment or emulsify the nucleus of the cataract-effected lens. Once fragmented or emulsified, the nuclear material is aspirated through a lumen of the phaco-emulsification needle.

During aspiration of the fragmented nucleus, a simultaneous flow of liquid into the eye is provided around the needle via a soft plastic or elastomeric sleeve concentrically disposed over the needle to form an annulus. This flow of liquid into the eye is essential to prevent collapse of the anterior chamber of the eye while the fragmented or emulsified nucleus is aspirated via the phaco-emulsification needle. Also, the inflowing liquid serves to cool the needle, thus reducing heat generated by the ultrasonic vibration of the needle. If this heat were instead permitted to be transmitted to the entry wound of the eye, thermal damage of the cornea or scleral tissue could result.

One difficulty encountered in practicing the phaco-emulsification technique is the necessity of maintaining a low-leakage seal between the entry wound in the eye and the sleeve surrounding the phaco-emulsification needle. If the wound entrance is too small, the sleeve may be compressed against the needle, thereby restricting the flow of irrigant into the anterior chamber and allowing frictional heat to be transmitted to the wound.

Alternatively, if the wound is made large to avoid compression of the sleeve, unacceptably high leakage may occur around the sleeve, for example, at rates of 25 cc/minute. The liquid lost by leakage must be replaced by liquid inflow through the annulus between the plastic sleeve and the needle, thus reducing the safety margin in maintaining a constant anterior chamber volume. Accordingly, to avoid collapse of the anterior chamber, liquid inflow through the annulus should never be less than total liquid outflow via the phaco-emulsification lumen and leakage around the sleeve.

In response to these concerns, a number of techniques have been developed which attempt to reduce leakage from the wound by improving the seal between the wound and the sleeve, while avoiding heat transmission to the wound.

A first technique uses a rigid plastic sleeve made from a material such as polysulphone rather than a softer silicone material, because polysulphone resists compression by the wound. Another technique, described in U.S. Pat. No. 5,282,786, incorporates a rigid plastic or metal sleeve disposed on the outer circumference of a softer silicon sleeve, so that the rigid plastic contacts the entry wound. These techniques, however, have the drawback that they increase wound distortion and tend to enlarge the wound during the procedure, thus enhancing leakage.

A second technique, described for example in U.S. Pat. Nos. 5,286,256 and 5,354,265, employs a rigid plastic or metal intermediate sleeve inserted in the annulus between the conventional outer soft silicone sleeve and the phaco-emulsification needle. The rigid intermediate sleeve is permitted to "float" on the exterior of the phaco-emulsification needle, and the needle may have a reduced outer diameter in a middle region to limit longitudinal travel of the intermediate sleeve. The reduced middle region of the needle permits a small incision while maintaining fluid flow around the phaco-emulsification needle. However, such benefits are believed to be more than offset by the increase in the overall diameter of the apparatus to accommodate the intermediate sleeve and the overall reduction in the irrigation cross-sectional flow area caused by the presence of the intermediate sleeve.

A yet third technique attempting to solve the problems of fluid leakage from the entry wound and heat transmission is described in U.S. Pat. Nos. 4,634,420, 4,643,717, 4,808,154 and 5,242,385. The sleeves described in these patents each include a plurality of inwardly extending ribs that serve to reinforce the sleeve against compression, to limit contact between the sleeve and the phaco-emulsification needle, and to provide flow channels in the event that the sleeve is compressed against the needle. All of these designs share the common drawback that the ribs enhance the rigidity of the sleeve, and thus pose a risk of transmitting more frictional heat to the entry wound. In addition, all of these designs require a larger entry wound to accommodate the added dimension of the ribs. Moreover, if the ribs are formed of silicone or other soft plastic or elastomeric material, it is expected that the compressive loads transmitted to such sleeves from the entry wound may compress the ribs to an extent that unacceptably low flow rates might still occur.

In view of the foregoing, it would be desirable to provide a phaco-emulsification needle that overcomes the drawbacks of previously known needle and sleeve arrangements by permitting the use of a small wound size, and that reduces the risk of restriction of fluid flow around the needle.

It further would be desirable to provide a phaco-emulsification needle that provides reduced contact area between the needle and the sleeve, thus reducing the transmission of heat to adjacent tissue, with concomitant reduction in the risk of tissue damage.

It would be still further desirable to provide a phaco-emulsification needle that ensures adequate irrigant flow even in those cases where the sleeve is compressed against the exterior of the needle.

It would be yet further desirable to provide a device for use with a phaco-emulsification needle that would improve fluid flow and reduce heat transmission in those cases where the sleeve is subjected to high compressive loading by the entry wound.

SUMMARY OF THE INVENTION

In view of the foregoing, it is an object of the present invention to provide a phaco-emulsification needle that overcomes the drawbacks of previously known needle and sleeve arrangements by permitting the use of a small wound size, and that reduces the risk of restriction of fluid flow around the needle.

It is a further object of the invention to provide a phaco-emulsification needle that provides reduced contact area between the needle and the sleeve, thus reducing the transmission of heat to adjacent tissue, with concomitant reduction in the risk of tissue damage.

It is still a further object of the present invention to provide a phaco-emulsification needle that ensures adequate irrigant flow even in those cases where the sleeve is compressed against the exterior of the needle.

It is yet another object of this invention to provide a device for use with a phaco-emulsification needle that improves fluid flow and reduces heat transmission in those cases where the sleeve is subjected to high compressive loading by the entry wound.

These and other objects of the invention are accomplished in accordance with the principles of the present invention by providing a phaco-emulsification needle comprising a shaft having an axially extending lumen for removal of material from an eye, and at least in a middle region of the needle, one or more axially extending channels or grooves disposed externally of the lumen for supplying fluid to the eye during aspiration.

With the phaco-emulsification needle of the present invention, even if a soft plastic or elastomeric sleeve is compressed against the needle, the channels or grooves permit continued fluid flow while reducing the contact area between the sleeve and needle, thereby reducing the risk of thermal damage to the entry wound.

In a second embodiment of the present invention, a sleeve having a plurality of outwardly extending projections is provided that may be disposed on the exterior surface of a phaco-emulsification needle. The sleeve of the second embodiment may be disposed in a reduced circumference mid-region of the needle to provide benefits similar to those of the first embodiment described hereinabove.

Further features of the invention, its nature and various advantages will be more apparent from the accompanying drawings and the following detailed description of the preferred embodiments.

DETAILED DESCRIPTION OF THE PREFERRED EMBODIMENTS

Figure 1:
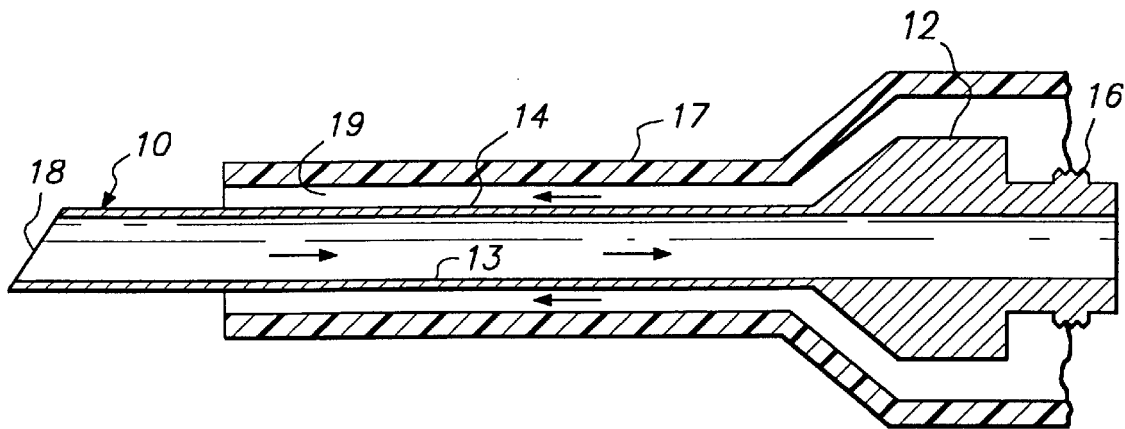
FIG. 1 is a side elevation of a previously known phaco-emulsification needle.

Referring to FIG. 1, a previously known phaco-emulsification needle 10 is shown comprising hub 12 and hollow shaft 14 extending from hub 12. A threaded portion 16 extends away from hub 12 on the proximal portion of shaft 14, as is conventional. Shaft 14 terminates in tip 18 at the distal end (i.e., remote from hub 12).

Needle 10 contains a central axially extending lumen 13 through which material can be drawn from an eye using known techniques, as described hereinabove. Sleeve 17, which typically comprises a soft silicone material, is disposed over needle 10 to form an annulus 19 through which liquid can be supplied to the anterior chamber of the eye during aspiration. As further described hereinabove, sleeve 17 can be compressed by the eye, and in particular, the portion surrounding the entry wound, to reduce liquid flow to an unacceptable extent.

Figure 2A:
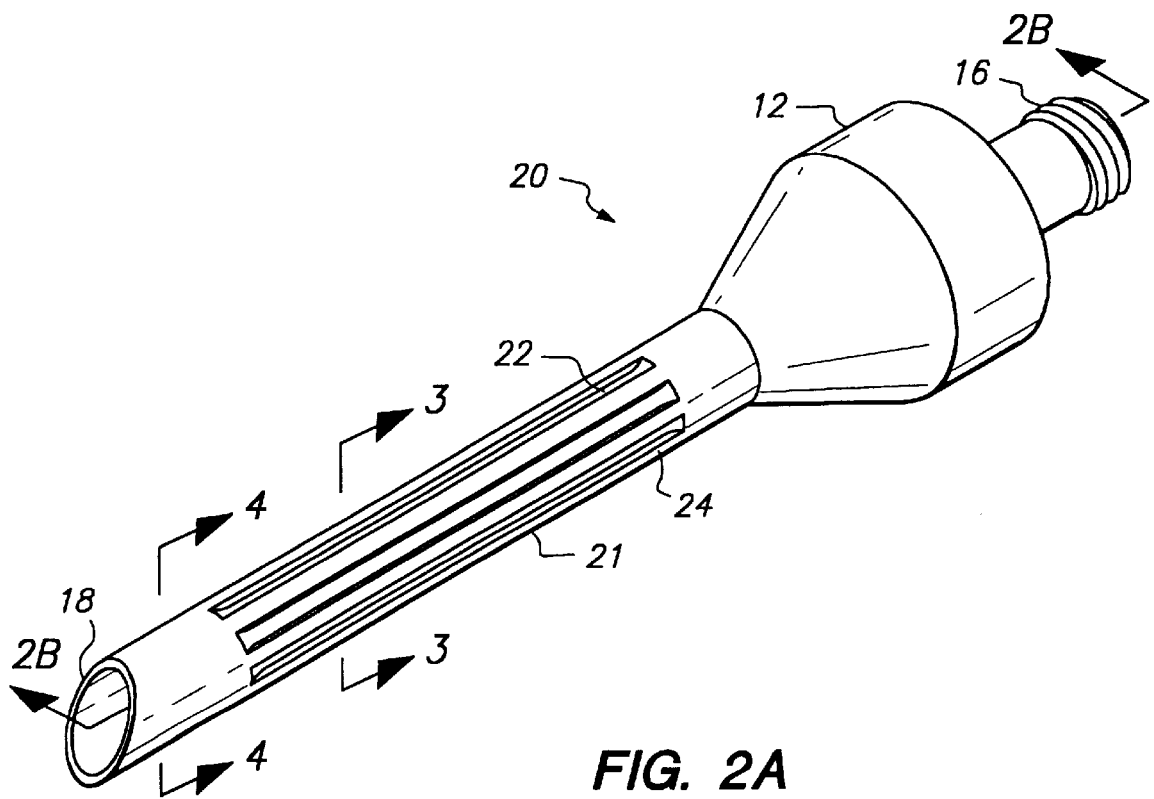
FIG. 2A is a perspective view of a phaco-emulsification needle constructed in accordance with the present invention.
Figure 2B:
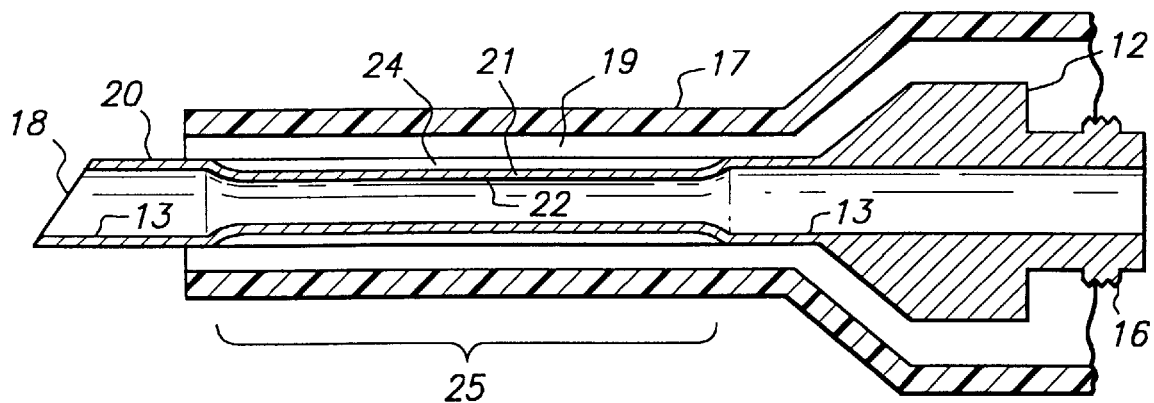
FIG. 2B is a sectional view taken along line 2B—2B of the phaco-emulsification needle of FIG. 2A, showing the needle disposed within a sleeve.

Referring now to FIGS. 2A and 2B, phaco-emulsification needle 20 constructed in accordance with the present invention is described, in which like numbers denote like parts. As will of course be understood by one of skill in the art, FIGS. 2A and 2B are not drawn to scale, but are provided merely for illustration. Needle 20, which is typically made of titanium, comprises hub 12, lumen 13, threaded portion 16, tip 18 and tubular portion 21 located in mid-region 25 between tip 18 and hub 12.

Figure 3:
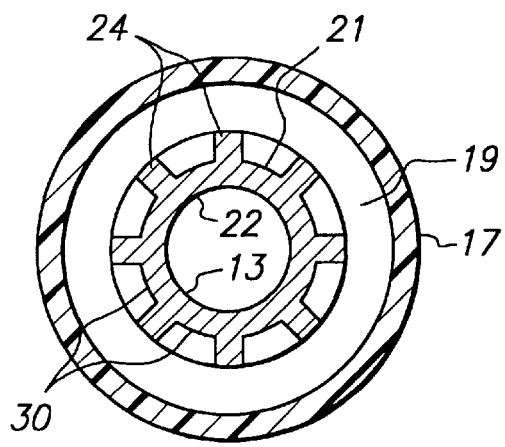
FIG. 3 is an enlarged cross-sectional view taken along the line 3—3 of FIG. 2A.

Referring now also to FIG. 3, tubular portion 21 illustratively comprises hollow reduced-circumference cylindrical member 22 having a plurality of equispaced rib-like projections or flanges 24 extending radially outwardly from the outer surface of member 22. As shown in FIG. 2B, if projections 24 in mid-region 25 are alternatively viewed from the perspective of the outer diameter of the adjacent proximal and distal regions, the interstices between adjacent projections 24 appear as longitudinally-oriented channels or grooves 30 in the outer surface of needle 20.

Figure 4:
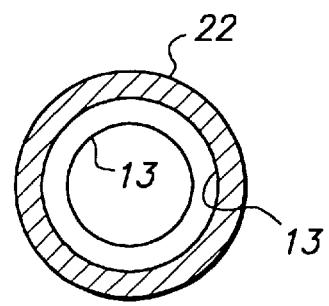
FIG. 4 is an enlarged cross-sectional view taken along the line 4—4 of FIG. 2A.

Projections 24 on reduced-circumference cylindrical member 22 may have their outer surfaces formed flush with the outer surface of needle 20 in the regions proximal and distal to mid-region 25 (as in FIG. 2B), or extend slightly below or beyond the outer surface of needle 20 in the adjacent proximal and distal regions. To accommodate projections 24 (and thus grooves 30), lumen 13 may have a reduced diameter in central region 25, as can be seen by comparison of FIGS. 3 and 4. Projections 24 and reduced-circumference cylindrical member 22 may be disposed only in central or mid-region 25 of needle 20, which is the region typically subjected to compressive loading by the tissue surrounding the entry wound, or may alternatively extend along the entire outer surface of needle 20 to tip 18.

Disposed about and spaced from tubular portion 21 is sleeve 17, which may be formed of soft plastic or elastomeric material, for example, silicone. When sleeve tube 17 is subjected to a compressive load and contacts needle 20, adjacent projections 24, together with the intervening portion of reduced-circumference cylindrical member 22 and the inner surface of sleeve 17, form channels or grooves 30 which extend axially along needle 20.

Accordingly, if needle 20 comes under pressure along its mid-region 25 during a procedure of removing a cataract-effected lens, reduction in the cross-sectional areas of the channels 30 is inhibited by the presence of projections 24. Liquid flow through the sleeve 17 via channels 30 therefore can be maintained at a satisfactory level to replenish liquid removed by aspiration in the anterior chamber of the eye.

Moreover, no special external sleeves are required to ensure adequate irrigation using needle 20. Thus, sealing between the sleeve 17 and entry wound may be accomplished with a previously known sleeve 17 as described with respect to FIG. 1, while maintaining the required wound size in the desired 2.5–3.2 mm range.

Tubular portion 21 may be of a variety of shapes in cross-section, including circular and elliptical, and may have an outer circumference that is smaller than, the same as, or larger than the circumference of the adjacent proximal and distal portions of needle 20. In addition, central lumen 13 of needle 20 may have a single diameter over its entire length, or may be formed having a reduced diameter in the mid-region of tubular portion 21.

Likewise, projections 24 (and grooves 30) may be greater or fewer in number than shown in the accompanying figures, and form greater or lesser portions of the outer circumference of central portion 25 than shown in the accompanying figures, which are to be understood as exemplary only. Moreover, projections 24 need not be spaced equidistant apart around the circumference of tubular portion 21, but may instead be concentrated on the upper and lower portions of needle 20, which are most likely to experience compressive loads.

Figure 5:
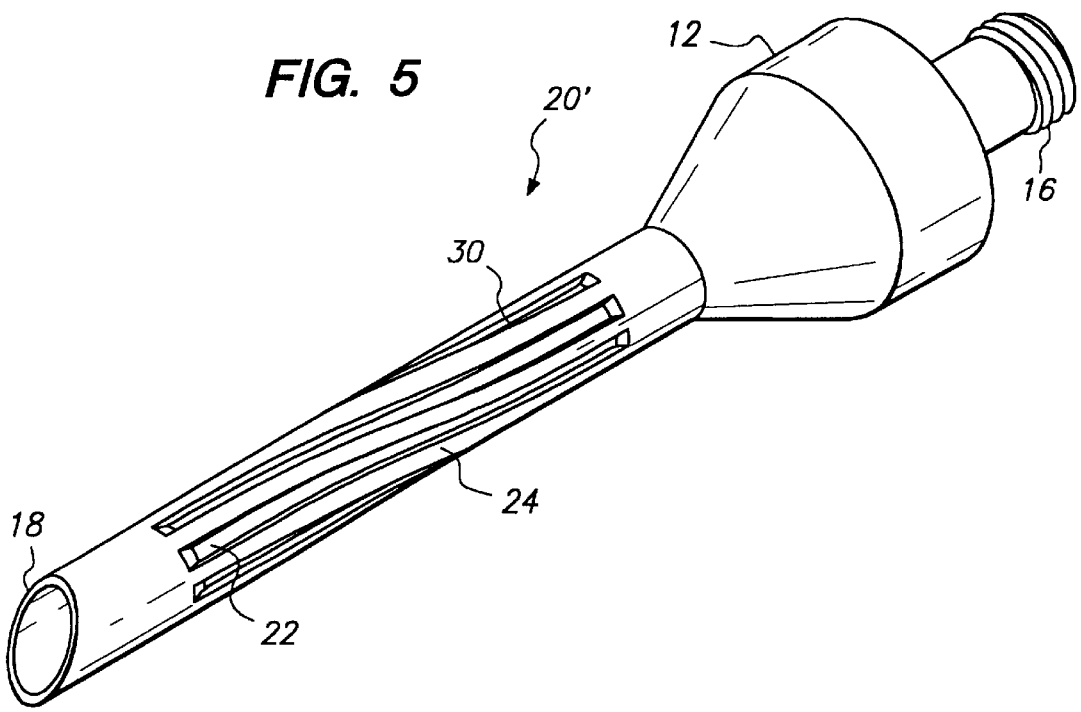
FIG. 5 is a perspective view of an alternative embodiment of the phaco-emulsification needle of FIG. 2A.
Figure 6:
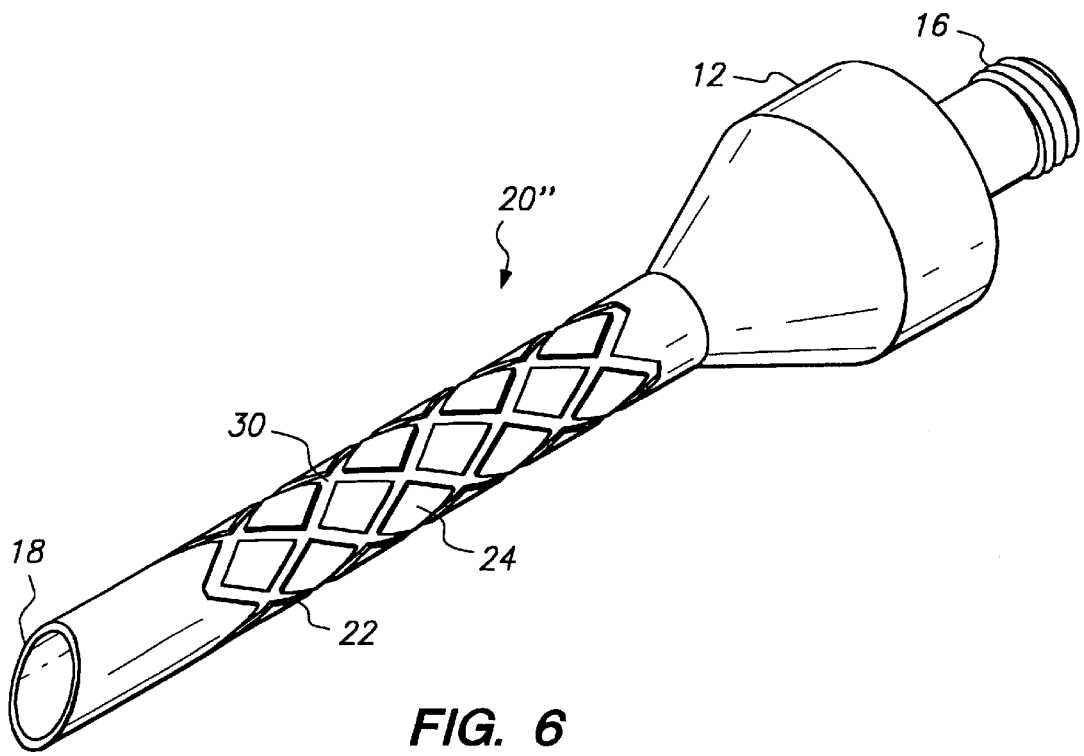
FIG. 6 is a perspective view of another alternative embodiment of the phaco-emulsification needle of FIG. 2A.

Referring now to FIGS. 5 and 6, alternative embodiments of the phaco-emulsification needle of the present invention are shown, again in which like numbers denote like parts. In FIG. 5, needle 20' has longitudinally-oriented projections 24 that spiral around the circumference of cylindrical member 22, thereby creating spiral channels.

In FIG. 6, projections 24 on needle 20 are formed as individual longitudinally-oriented diamond-shaped islands extending outward from the outer circumference of cylindrical member 22, for example, by cross-cutting reverse-spiral grooves in the needle of FIG. 5. As will of course be understood by one of skill in the art, grooves 30 may be disposed in a needles 20' and 20" by rotating the needle as the grooves 30 are being formed.

In a preferred embodiment of the needle of FIGS. 2–6, projections 24 and cylindrical member 22 may be formed by machining a single piece of titanium to the desired shape. Alternatively, a phaco-emulsification needle in accordance with the present invention may be formed from stainless steel, a suitably tough plastic composite, or a combination thereof. Likewise, projections 24 may be formed in any of a number of readily manufacturable configurations, for example, as circumferential channels with longitudinally-oriented communications, or even cylindrical nub-like shapes.

Figure 7A:
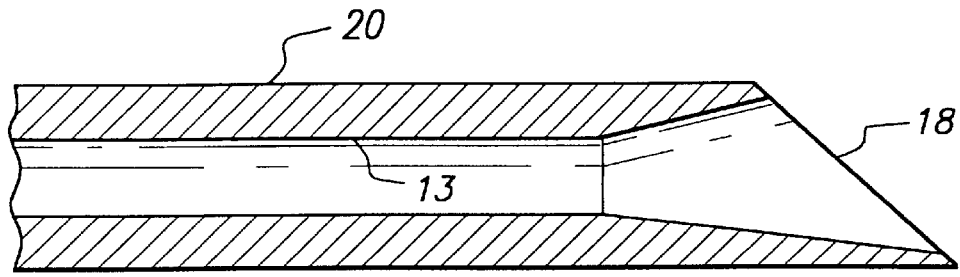
FIGS. 7A through 7D are alternative designs for tip 18 of any of the phaco-emulsification needles of the present invention.
Figure 7B:
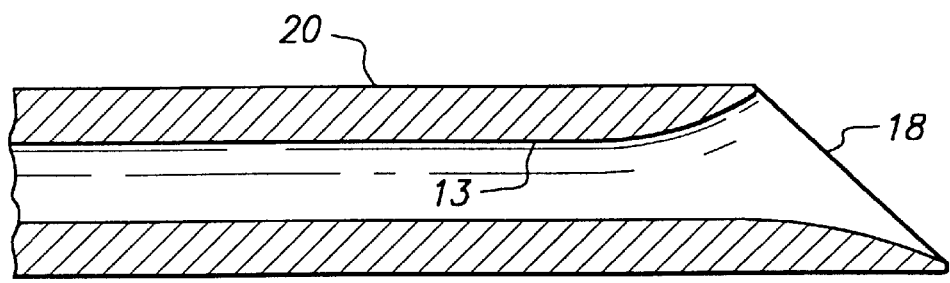
Figure 7C:
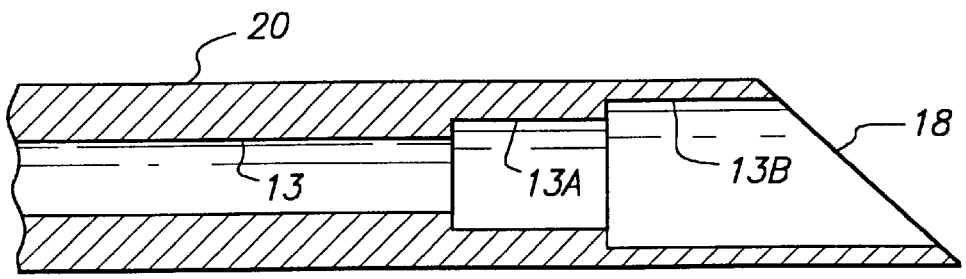
Figure 7D:
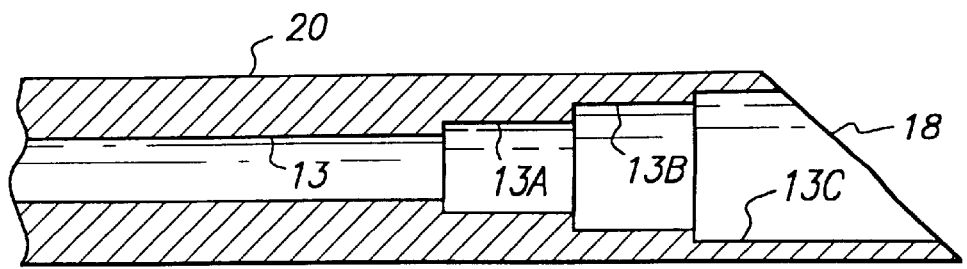

Referring now to FIGS. 7A through 7D, alternative designs of tip 18 of needle 20 are illustrated. FIG. 7A shows lumen 13 in the distal portion of needle 20 expanding to tip 18 in a funnel-like manner; FIG. 7B shows the lumen 13 having a curved horn-like shape as it expands to tip 18. FIGS. 7C and 7D illustrate alternative embodiments in which lumen 13 expands to tip 18 through a series of multi-chamber steps 13A–13B and 13A–13C. The foregoing lumen and tip configurations may be advantageously used with any of the phaco-emulsification needles of the present invention.

Figure 8A:
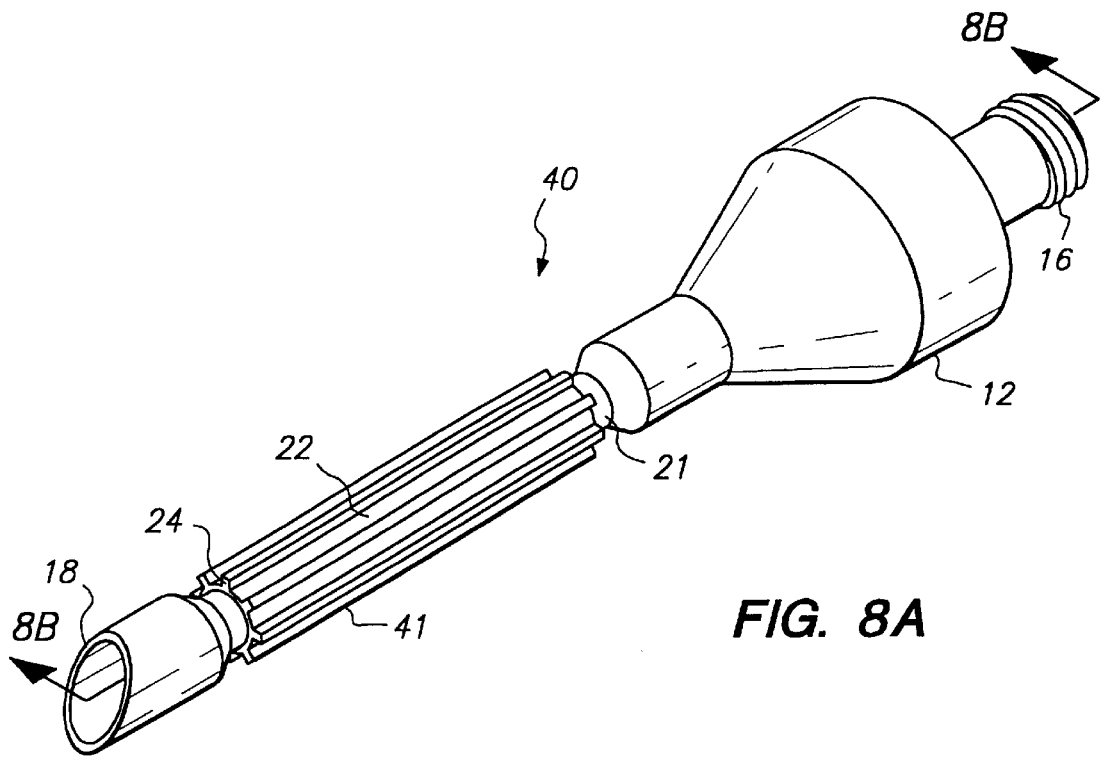
FIG. 8A is a perspective view of a ribbed sleeve and phaco-emulsification needle in accordance with another alternative embodiment of the present invention.
Figure 8B:
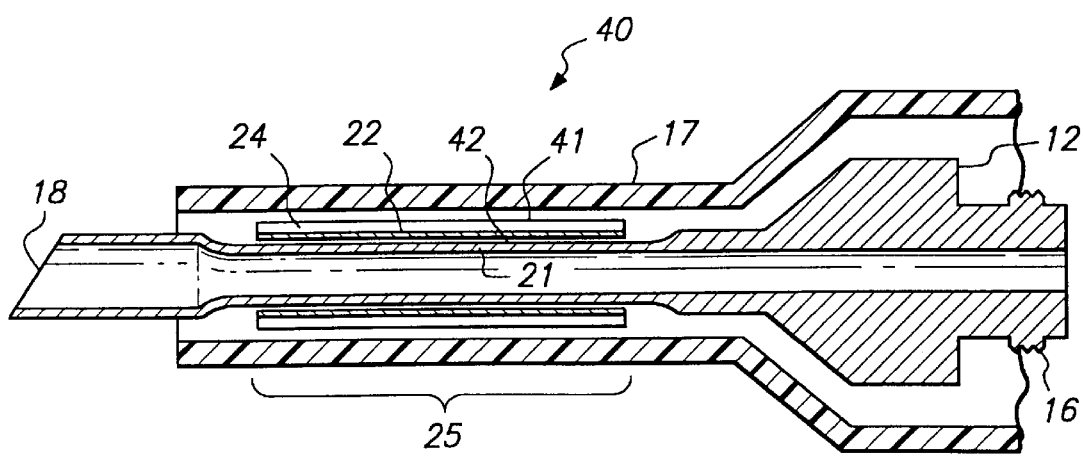
FIG. 8B is a sectional view taken along line 8B—8B of the phaco-emulsification needle of FIG. 8A, showing the needle disposed within a sleeve.

Referring now to FIGS. 8A and 8B, another alternative embodiment of the phaco-emulsification needle of the present invention, needle 40, is described, again in which like numbers denote like parts. Needle 40 includes reduced-circumference portion 21 in mid-region 25. Flanges or projections 24 and cylindrical member 22 form a separate insert 41 which is disposed on the reduced-circumference portion 21 of needle 40.

Insert 41 may be formed of a soft plastic or elastomeric material, for example, silicone, and preferably is dimensioned so that gap 42 forms between the inner surface of cylindrical member 22 and the outer surface of reduced-circumference portion 21. Cylindrical member 22 may also include a longitudinal slit that permits cylindrical member 22 to be easily installed over reduced-circumference portion 21.

Alternatively, cylindrical member 22 may be dimensioned to slip over a standard phaco-emulsification needle 10 as shown in FIG. 1, but may then require the use of a larger sleeve 17 and larger entry wound. When installed on the either reduced-circumference portion 21 of needle 40 or standard needle 10, insert 41 is expected to provide many of the advantages described hereinabove with respect to the needle embodiments of FIGS. 2–6.

Applicant has performed some closed chamber experiments employing a silicone model "eye" used in phaco-emulsification training workshops, in which the silicone "cornea" can be exchanged. In particular, applicant used a Series 10000 Master phaco-emulsification system, available from Alcon Surgical, Fort Worth, Tex., to compare the cooling performance of a needle constructed in accordance with the embodiment of FIG. 2 to a standard Master phaco-emulsification needle.

The experiments were conducted using a power setting of 70 on the Master system, a vacuum setting of 100 mmHg, a bottle height of 65 cm, an irrigant flow rate 20 cc/min and an initial irrigant temperature of 25.6° C. Varying the incision size from 2.75 mm to 4.1 mm in the silicone cornea (obtained using a keratome), the temperature of the sleeve at the point of compression by the incision was measured with a thermocouple for both the standard needle and the needle of FIG. 2 after 15 seconds of operation. The results are shown in Table 1.

TABLE 1

| Incision Size (mm) | Sleeve Temperature ° C. | |
|---|---|---|
| | Standard Needle | FIG. 2 Needle |
| 2.75 | 53 | 37 |
| 3.00 | 50 | 32 |
| 3.25 | 47 | 32 |
| 3.50 | 44 | 30 |
| 4.10 | 33 | 28 |

As will be observed from Table 1, the sleeve temperature was lower for the needle of FIG. 2 at all incision sizes and always remained below 40° C. In contrast, using the standard tip, the sleeve reached temperature levels exceeding fifty degrees—a temperature at which thermal damage and collagen shrinkage would be expected to occur.

Applicant performed similar experiments in which the incision size was maintained at 3.00 mm and the flow rate was varied from 20 to 35 cc/min. While the performance of neither the standard needle nor the needle of FIG. 2 varied much with change in irrigant flow rate, the sleeve temperature for the needle of FIG. 2 was consistently about 20° C. lower than for the standard needle. In yet a third series of experiments, applicant kept the incision size at 3.00 mm and the flow rate constant at 20 cc/min and varied the irrigant bottle height from 65 to 75 cm. This also did not produce much of an effect in the sleeve temperature for either needle, but again the sleeve temperature for the needle of FIG. 2 was consistently about 20° C. lower than for the standard needle.

While preferred illustrative embodiments of the present invention are described above, it will be obvious to one skilled in the art that various changes and modifications may be made therein without departing from the invention and it is intended in the appended claims to cover all such changes and modifications which fall within the true spirit and scope of the invention.

What is claimed is:

1. A phaco-emulsification needle and sleeve by which an irritant is supplied to a patient's eye through an incision, the phaco-emulsification needle and sleeve comprising:

a shaft disposed within the sleeve and having a proximal end, a distal end, and a first circumference, a mid-region having a second circumference and a plurality of longitudinally-oriented outwardly extending projections disposed from the second circumference, and a longitudinal lumen extending through the shaft from the proximal end to the distal end;

a hub disposed at the proximal end of the shaft having means for engaging a phaco-emulsification tool, the longitudinal lumen extending through the hub; and a tip disposed at the distal end of the shaft, the tip having an opening communicating with longitudinal lumen, wherein, when the phaco-emulsification needle is connected to a phaco-emulsification tool, the longitudinally-oriented outwardly extending projections form fluid channels that maintain irrigant flow from the proximal end to the distal end and into the patient's eye even when the sleeve is compressed against the incision, irrigant being removed from the patient's eye through the longitudinal lumen via the opening at the tip.

2. The phaco-emulsification needle and sleeve as defined in claim 1, wherein the second circumference is different than the first circumference.

3. The phaco-emulsification needle and sleeve as defined in claim 2, wherein the second circumference is smaller than the first circumference.

4. The phaco-emulsification needle and sleeve as defined in claim 3, wherein the projections have an outer diameter, and the outer diameter of the projections is flush with the first circumference.

5. The phaco-emulsification needle and sleeve as defined in claim 1, wherein the longitudinal lumen has a first cross-sectional area and, in the mid-region, the lumen has a second cross-sectional area smaller than the first cross-sectional area.

6. The phaco-emulsification needle and sleeve as defined in claim 1, wherein the outwardly extending projections form a plurality of ribs.

7. The phaco-emulsification needle and sleeve as defined in claim 6, wherein the plurality of ribs are mutually parallel.

8. The phaco-emulsification needle and sleeve as defined in claim 7, wherein the plurality of ribs spiral around the second circumference.

9. The phaco-emulsification needle and sleeve as defined in claim 6, wherein the plurality of ribs is spaced apart equidistant around the second circumference.

10. The phaco-emulsification needle and sleeve as defined in claim 6, wherein the plurality of ribs define a plurality of grooves in communication with one another.

11. The phaco-emulsification needle and sleeve as defined in claim 1, wherein the plurality of outwardly extending projections extend radially outward from the second circumference.

12. The phaco-emulsification needle and sleeve as defined in claim 1 wherein the shaft is cylindrical.

13. The phaco-emulsification needle and sleeve as defined in claim 1 wherein the longitudinal lumen expands to the tip in a shape selected from the group consisting of a funnel-shape, a horn-shape and a multi-chambered stepped-shape.

14. The phaco-emulsification needle and sleeve as defined in claim 1 wherein the phaco-emulsification needle is machined from a single piece of titanium.

15. A phaco-emulsification needle and sleeve by which an irrigant is supplied to a patient's eye through an incision, the phaco-emulsification needle and sleeve comprising:

a shaft disposed within the sleeve and having a proximal end, a distal end, and an outer circumference, a mid-region comprising a portion having a plurality of longitudinally-oriented grooves in the outer circumference of the shaft, and a longitudinal lumen extending through the shaft from the proximal end to the distal end;

a hub disposed at the proximal end of the shaft having means for engaging a phaco-emulsification tool, the longitudinal lumen extending through the hub; and a tip disposed at the distal end of the shaft, the tip having an opening communicating with longitudinal lumen, wherein, when the needle is connected to the phaco-emulsification tool, the longitudinally-oriented grooves form fluid channels that enable a sufficient amount of irrigant to flow between the phaco-emulsification needle and the sleeve to maintain a peak local temperature of the sleeve below 40° C., even when the sleeve is compressed against the incision.

16. The phaco-emulsification needle and sleeve as defined in claim 15, wherein the longitudinal lumen has a first cross-sectional area and, in the mid-region, the lumen has a second cross-sectional area smaller than the first cross-sectional area.

17. The phaco-emulsification needle and sleeve as defined in claim 15, wherein the plurality of longitudinally extending grooves is spaced apart equidistant around the outer circumference of the mid-region.

18. The phaco-emulsification needle and sleeve as defined in claim 15, wherein the plurality of longitudinally extending grooves are aligned in a mutually parallel relation.

19. The phaco-emulsification needle and sleeve as defined in claim 18, wherein the plurality of longitudinally extending grooves spiral around the mid-region.

20. The phaco-emulsification needle and sleeve as defined in claim 15, wherein the plurality of longitudinally extending grooves are in communication with one another.

21. The phaco-emulsification needle and sleeve as defined in claim 15 wherein the shaft is cylindrical.

22. The phaco-emulsification needle and sleeve as defined in claim 15 wherein the phaco-emulsification needle is machined from a single piece of titanium.

23. The phaco-emulsification needle and sleeve as defined in claim 15 wherein the longitudinal lumen expands to the tip in a shape selected from the group consisting of a funnel-shape, a horn-shape and a multi-chambered stepped-shape.

\* \* \* \* \*